US012471900B2

(12) United States Patent
VanWagner et al.

(10) Patent No.: US 12,471,900 B2
(45) Date of Patent: Nov. 18, 2025

(54) SURGICAL RETRACTOR AND BIDIRECTIONAL RATCHET

(71) Applicant: Thompson Surgical Instruments, Inc., Traverse City, MI (US)

(72) Inventors: Paul VanWagner, Kingsley, MI (US); Adam Francis, Traverse City, MI (US); William White, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 0 days.

(21) Appl. No.: 18/677,083

(22) Filed: May 29, 2024

(65) Prior Publication Data

US 2024/0398396 A1 Dec. 5, 2024

Related U.S. Application Data

(60) Provisional application No. 63/470,237, filed on Jun. 1, 2023.

(51) Int. Cl.
*A61B 17/02* (2006.01)
*A61B 17/00* (2006.01)

(52) U.S. Cl.
CPC .................... *A61B 17/0206* (2013.01); *A61B 2017/00407* (2013.01)

(58) Field of Classification Search
CPC . A61B 17/02; A61B 17/0206; A61B 17/0218; A61B 17/025
See application file for complete search history.

(56) References Cited

U.S. PATENT DOCUMENTS

| | | | |
|---|---|---|---|
| 3,749,088 | A | 7/1973 | Kohlmann |
| 4,957,495 | A | 9/1990 | Kluger |
| 4,971,038 | A | 11/1990 | Farley |
| 5,059,194 | A | 10/1991 | Michelson |
| 5,219,349 | A | 6/1993 | Krag et al. |
| 5,902,233 | A | 5/1999 | Farley et al. |
| 5,931,777 | A | 8/1999 | Sava |
| 5,944,658 | A | 8/1999 | Koros et al. |
| 5,984,865 | A | 11/1999 | Farley et al. |
| 5,984,867 | A | 11/1999 | Deckman et al. |

(Continued)

FOREIGN PATENT DOCUMENTS

| | | |
|---|---|---|
| EP | 1269922 | 1/2003 |
| ES | 2272170 | 4/2007 |

(Continued)

OTHER PUBLICATIONS

International Search Report and Written Opinion for Application No. PCT/US2024/31616, mailed Sep. 10, 2024, 6 pages.

*Primary Examiner* — Si Ming Ku
(74) *Attorney, Agent, or Firm* — McAndrews, Held & Malloy, Ltd.

(57) ABSTRACT

A surgical device includes a ratchet having pawls biased to a locked position in which the pawls prevent movement of a ratchet body along a rack. A pinion and a cam disc of the ratchet cooperate to selectively release the pawls from the rack and impart ratcheted movement of the ratchet body along the rack. Rotation of a handle rotates the pinion and the cam disc. Due to such rotation, the cam disc periodically releases the pawls from the rack, and the pinion imparts movement of the ratchet body along the rack during the periodic release of the pawls.

20 Claims, 11 Drawing Sheets

(56) References Cited

U.S. PATENT DOCUMENTS

| | | | |
|---|---|---|---|
| 6,036,641 | A | 3/2000 | Taylor et al. |
| 6,139,493 | A | 10/2000 | Koros et al. |
| 6,468,207 | B1 | 10/2002 | Fowler, Jr. |
| 6,648,891 | B2 | 11/2003 | Kim |
| 6,887,198 | B2 | 5/2005 | Phillips et al. |
| 7,060,975 | B2 | 6/2006 | Seaward et al. |
| 7,173,240 | B2 | 2/2007 | Seaward et al. |
| 7,182,731 | B2 | 2/2007 | Nguyen et al. |
| 7,318,817 | B2 | 1/2008 | Hamada |
| 7,338,442 | B2 | 3/2008 | Mulac et al. |
| D566,269 | S | 4/2008 | Koros et al. |
| 7,491,168 | B2 | 2/2009 | Raymond et al. |
| 7,494,463 | B2 | 2/2009 | Nehls |
| 7,578,822 | B2 | 8/2009 | Rezach et al. |
| 7,618,424 | B2 | 11/2009 | Wilcox et al. |
| 7,850,608 | B2 | 12/2010 | Hamada |
| 7,883,522 | B2 | 2/2011 | Hamada |
| 7,887,482 | B2 | 2/2011 | Hamada |
| 7,892,174 | B2 | 2/2011 | Hestad et al. |
| 7,935,054 | B2 | 5/2011 | Hamada |
| 7,946,982 | B2 | 5/2011 | Hamada |
| 8,038,611 | B2 | 10/2011 | Raymond et al. |
| 8,100,828 | B2 | 1/2012 | Frey et al. |
| 8,114,020 | B2 | 2/2012 | Fricke et al. |
| 8,118,737 | B2 | 2/2012 | Perez-Cruet et al. |
| 8,172,849 | B2 | 5/2012 | Noon et al. |
| 8,192,440 | B2 | 6/2012 | Jones et al. |
| 8,197,488 | B2 | 6/2012 | Sorrenti et al. |
| 8,257,255 | B2 | 9/2012 | Farley et al. |
| 8,262,679 | B2 | 9/2012 | Nguyen |
| 8,267,945 | B2 | 9/2012 | Nguyen et al. |
| 8,357,184 | B2 | 1/2013 | Woolley et al. |
| 8,496,673 | B2 | 7/2013 | Nguyen et al. |
| 8,506,479 | B2 | 8/2013 | Piskun et al. |
| 8,602,984 | B2 | 12/2013 | Raymond et al. |
| 8,622,897 | B2 | 1/2014 | Raymond et al. |
| 8,636,657 | B2 | 1/2014 | Hamada |
| 8,679,129 | B2 | 3/2014 | Sorrenti et al. |
| 8,696,562 | B2 | 4/2014 | Mulac et al. |
| 8,906,034 | B2 | 12/2014 | Gleeson et al. |
| 8,932,211 | B2 | 1/2015 | Piskun et al. |
| 9,060,757 | B2 | 6/2015 | Lawson et al. |
| 9,101,413 | B2 | 8/2015 | Masson et al. |
| 9,125,636 | B2 | 9/2015 | Piskun et al. |
| 9,125,703 | B2 | 9/2015 | McClintock et al. |
| 9,131,966 | B2 | 9/2015 | Solitario, Jr. et al. |
| 9,161,746 | B2 | 10/2015 | Piskun et al. |
| 9,179,947 | B2 | 11/2015 | Bass |
| 9,186,130 | B2 | 11/2015 | Piskun et al. |
| 9,186,131 | B2 | 11/2015 | Piskun et al. |
| 9,226,751 | B2 | 1/2016 | Shelton, IV et al. |
| 9,277,906 | B2 | 3/2016 | White |
| 9,320,506 | B2 | 4/2016 | Bertagnoli et al. |
| 9,364,230 | B2 | 6/2016 | Shelton, IV et al. |
| 9,408,606 | B2 | 8/2016 | Shelton, IV |
| 9,554,690 | B2 | 1/2017 | Piskun et al. |
| 9,565,998 | B2 | 2/2017 | Piskun et al. |
| 9,655,506 | B2 | 5/2017 | Piskun et al. |
| 9,713,416 | B2 | 7/2017 | Piskun et al. |
| 9,737,194 | B2 | 8/2017 | Piskun et al. |
| 10,258,333 | B2 | 4/2019 | Shelton, IV et al. |
| 10,383,630 | B2 | 8/2019 | Shelton, IV et al. |
| 10,485,541 | B2 | 11/2019 | Shelton, IV |
| 10,499,897 | B2 * | 12/2019 | Truckey ............. A61B 17/7077 |
| 10,517,580 | B2 | 12/2019 | Piskun et al. |
| 10,531,869 | B2 | 1/2020 | Piskun et al. |
| 10,537,238 | B2 | 1/2020 | Piskun et al. |
| 10,537,315 | B2 | 1/2020 | Piskun et al. |
| 10,548,582 | B2 | 2/2020 | Piskun et al. |
| 10,588,489 | B2 | 3/2020 | Piskun et al. |
| 10,588,504 | B2 | 3/2020 | Piskun et al. |
| 10,595,711 | B2 | 3/2020 | Piskun et al. |
| 10,595,841 | B2 | 3/2020 | Piskun et al. |
| 10,687,812 | B2 | 6/2020 | Shelton, IV et al. |
| 10,716,464 | B2 | 7/2020 | Piskun et al. |
| 10,758,116 | B2 | 9/2020 | Piskun |
| 10,869,657 | B2 | 12/2020 | Raymond et al. |
| 10,874,391 | B2 | 12/2020 | Shelton, IV et al. |
| 10,893,855 | B2 | 1/2021 | Truckey |
| RE48,485 | E | 3/2021 | Piskun et al. |
| 10,966,701 | B2 | 4/2021 | Piskun et al. |
| RE48,597 | E | 6/2021 | Piskun et al. |
| RE48,684 | E | 8/2021 | Piskun et al. |
| 11,083,457 | B2 | 8/2021 | Shelton, IV et al. |
| RE48,729 | E | 9/2021 | Piskun et al. |
| RE48,750 | E | 9/2021 | Piskun et al. |
| 11,122,970 | B2 | 9/2021 | Piskun et al. |
| 11,141,155 | B2 | 10/2021 | Shelton, IV |
| 11,141,156 | B2 | 10/2021 | Shelton, IV |
| 11,154,299 | B2 | 10/2021 | Shelton, IV et al. |
| RE48,800 | E | 11/2021 | Piskun et al. |
| RE48,850 | E | 12/2021 | Piskun et al. |
| 11,197,671 | B2 | 12/2021 | Shelton, IV et al. |
| 11,202,631 | B2 | 12/2021 | Shelton, IV et al. |
| 11,272,836 | B2 | 3/2022 | Piskun et al. |
| 11,278,199 | B2 | 3/2022 | Piskun et al. |
| 11,278,284 | B2 | 3/2022 | Shelton, IV et al. |
| 11,344,285 | B2 | 5/2022 | Piskun et al. |
| 11,406,256 | B2 | 8/2022 | Piskun et al. |
| 11,464,513 | B2 | 10/2022 | Shelton, IV et al. |
| 11,471,026 | B2 | 10/2022 | Piskun et al. |
| 2002/0026101 | A1 | 2/2002 | Bookwalter et al. |
| 2002/0095071 | A1 | 7/2002 | Farley |
| 2003/0004401 | A1 | 1/2003 | Ball et al. |
| 2003/0055430 | A1 | 3/2003 | Kim |
| 2003/0069478 | A1 | 4/2003 | Phillips et al. |
| 2004/0129109 | A1 | 7/2004 | Phillips et al. |
| 2004/0199055 | A1 | 10/2004 | Mulac et al. |
| 2004/0249388 | A1 | 12/2004 | Michelson |
| 2005/0021040 | A1 | 1/2005 | Bertagnoli |
| 2005/0113645 | A1 | 5/2005 | Sharratt et al. |
| 2005/0177028 | A1 | 8/2005 | Royce et al. |
| 2005/0192484 | A1 | 9/2005 | Sharratt et al. |
| 2005/0203533 | A1 | 9/2005 | Ferguson et al. |
| 2006/0224044 | A1 | 10/2006 | Marchek et al. |
| 2006/0247645 | A1 | 11/2006 | Wilcox et al. |
| 2007/0191856 | A1 | 8/2007 | Gil et al. |
| 2007/0270840 | A1 | 11/2007 | Chin et al. |
| 2008/0077155 | A1 | 3/2008 | Diederich et al. |
| 2008/0215081 | A1 | 9/2008 | Hsueh et al. |
| 2009/0221876 | A1 | 9/2009 | Cobb et al. |
| 2013/0023735 | A1 | 1/2013 | Brown et al. |
| 2014/0031874 | A1 | 1/2014 | Kucharzyk et al. |
| 2014/0107656 | A1 | 4/2014 | Masson et al. |
| 2015/0238177 | A1 | 8/2015 | Masson et al. |
| 2016/0128737 | A1 | 5/2016 | Coric et al. |
| 2018/0249992 | A1 | 9/2018 | Truckey |
| 2019/0142421 | A1 | 5/2019 | Shelton, IV |
| 2019/0321040 | A1 | 10/2019 | Shelton, IV |
| 2020/0060680 | A1 | 2/2020 | Shelton, IV et al. |
| 2020/0205651 | A1 | 7/2020 | Piskun et al. |
| 2020/0214686 | A1 | 7/2020 | Truckey et al. |
| 2020/0222038 | A1 | 7/2020 | Piskun et al. |
| 2020/0275927 | A1 | 9/2020 | Shelton, IV et al. |
| 2020/0352431 | A1 | 11/2020 | Piskun |
| 2022/0160222 | A1 | 5/2022 | Piskun et al. |
| 2022/0280032 | A1 | 9/2022 | Piskun et al. |
| 2022/0354360 | A1 | 11/2022 | Piskun et al. |

FOREIGN PATENT DOCUMENTS

| | | |
|---|---|---|
| FR | 2690067 | 10/1993 |
| FR | 2807313 | 10/2001 |
| GB | 1570499 | 7/1980 |

* cited by examiner

SURGICAL RETRACTOR AND BIDIRECTIONAL RATCHET

RELATED APPLICATIONS

This application claims benefit and priority to U.S. Provisional Patent Application No. 63/470,237, filed Jun. 1, 2023, the contents of the above-identified application is hereby incorporated herein by reference in its entirety.

BACKGROUND OF THE INVENTION

The present invention relates to systems and devices used during surgical procedures.

During a surgical procedure, a surgeon may make an incision in a patient to access internal organs, bones, and/or other anatomical structures. Retraction devices may be used to hold back soft tissue and other patient anatomy in the immediate area of the incision. Such retraction devices may provide the surgeon with an unobstructed view of the internal organs, bones, and/or other anatomical structures. Furthermore, the retraction devices may provide the surgeon with an opening via which the surgeon may access the anatomical structures with one or more surgical tools.

Limitations and disadvantages of conventional and traditional approaches should become apparent to one of skill in the art through comparison of such systems with aspects of the embodiments set forth in the remainder of the present disclosure.

BRIEF SUMMARY OF THE INVENTION

Retractor systems and devices are shown in and/or described in at least one figure of the present disclosure. Such retractor systems and/or devices of the present disclosure are set forth more completely in the claims. Advantages, aspects, novel features, as well as, details of illustrated embodiments may be more fully understood from the following description and figures.

For at least some embodiments, the retractor system and its components are drawn to scale in FIGS. 2-11.

DETAILED DESCRIPTION OF THE INVENTION

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non limiting and are generally synonymous with "by way of example and not limitation," "for example and not limitation," and the like.

As utilized herein, "and/or" means any one or more of the items in the list joined by "and/or". As an example, "x and/or y" means any element of the three element set {(x), (y), (x, y)}. In other words, "x and/or y" means "one or both of x and y." As another example, "x, y, and/or z" means any element of the seven element set {(x), (y), (z), (x, y), (x, z), (y, z), (x, y, z)}. In other words, "x, y and/or z" means "one or more of x, y, and z." Similarly, as utilized herein, "or" means any one or more of the items in the list joined by "or".

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, or components, but do not preclude the presence or addition of one or more other features, integers, steps, operations, elements, components, or groups thereof.

It will be understood that, although the terms first, second, etc. may be used herein to describe various elements, these elements should not be limited by these terms. These terms are only used to distinguish one element from another element. Thus, for example, a first element, a first component, or a first section discussed below could be termed a second element, a second component, or a second section without departing from the teachings of the present disclosure. Similarly, various spatial terms, such as "upper," "lower," "lateral," "side," "top," "bottom," and the like, may be used in distinguishing one element from another element in a relative manner. It should be understood, however, that components may be oriented in different manners, for example a component may be turned sideways so that its "top" surface is facing horizontally and its "lateral" or "side" surface is facing vertically, without departing from the teachings of the present disclosure.

Figure 1:
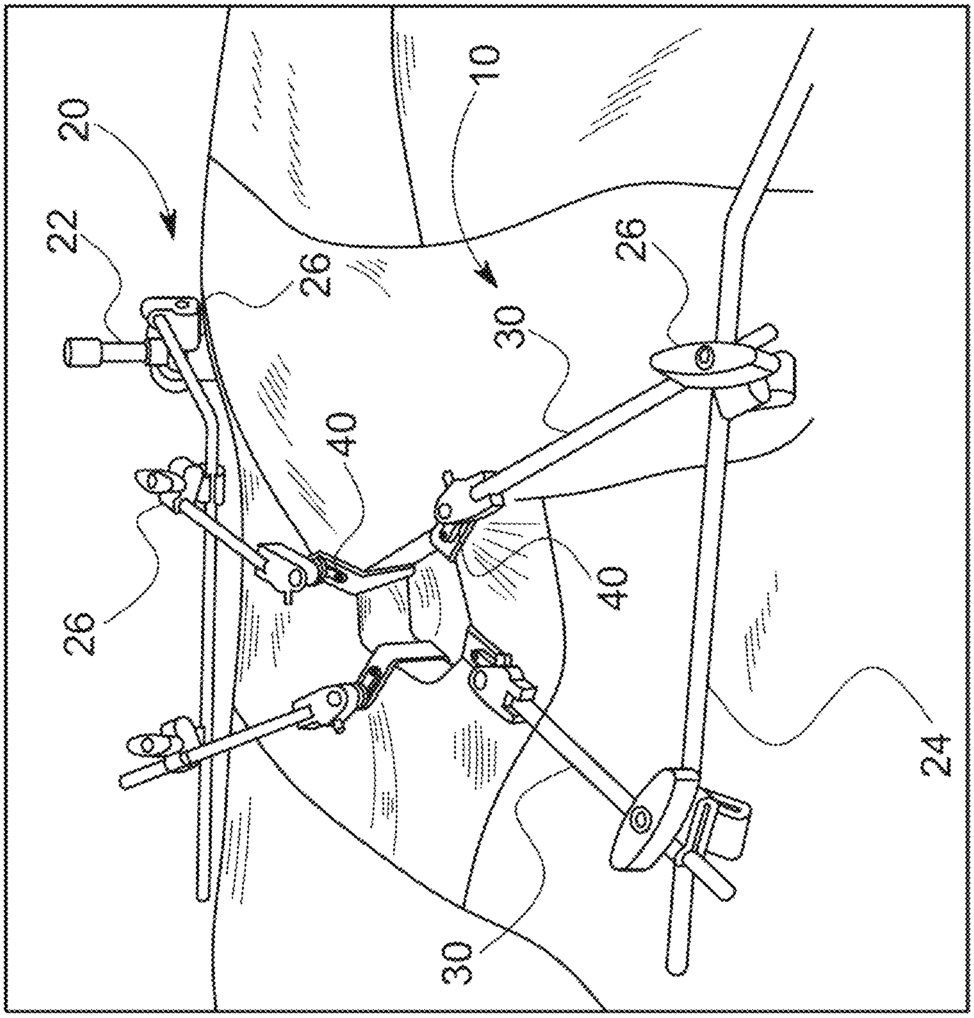
FIG. 1 provides a perspective view for a retractor system.

FIG. 1 illustrates an embodiment of a retractor system 10 in accordance with various aspects of the present disclosure. The retractor system 10 may include a frame assembly 20, a jointed arm 30, and a plurality of retractor blades 40. The various components of the retractor system 10 may be made, for example, of stainless steel.

The frame assembly 20 may include one or more posts 22, frame members 24, and clamps 26. Each post 22 may be fixed to a rail and/or a surgical table such that the post 22 extends upward in a generally vertical direction. Each post 22 may provide a location to which a frame member 24 may be secured. In the illustrated embodiment, two posts 22 are secured on opposite sides of a surgical tabled, with a frame member 24 secured to each post 22 by a clamp 26. In the illustrated embodiment, the frame members 24 are bent to extend toward the center of the hospital bed along a portion of their length. The frame members 24 may occupy a generally horizontal plane, and may provide a location to which to mount other components of the retractor system 10, such as jointed arms 30 via additional clamps 26.

Figure 2:
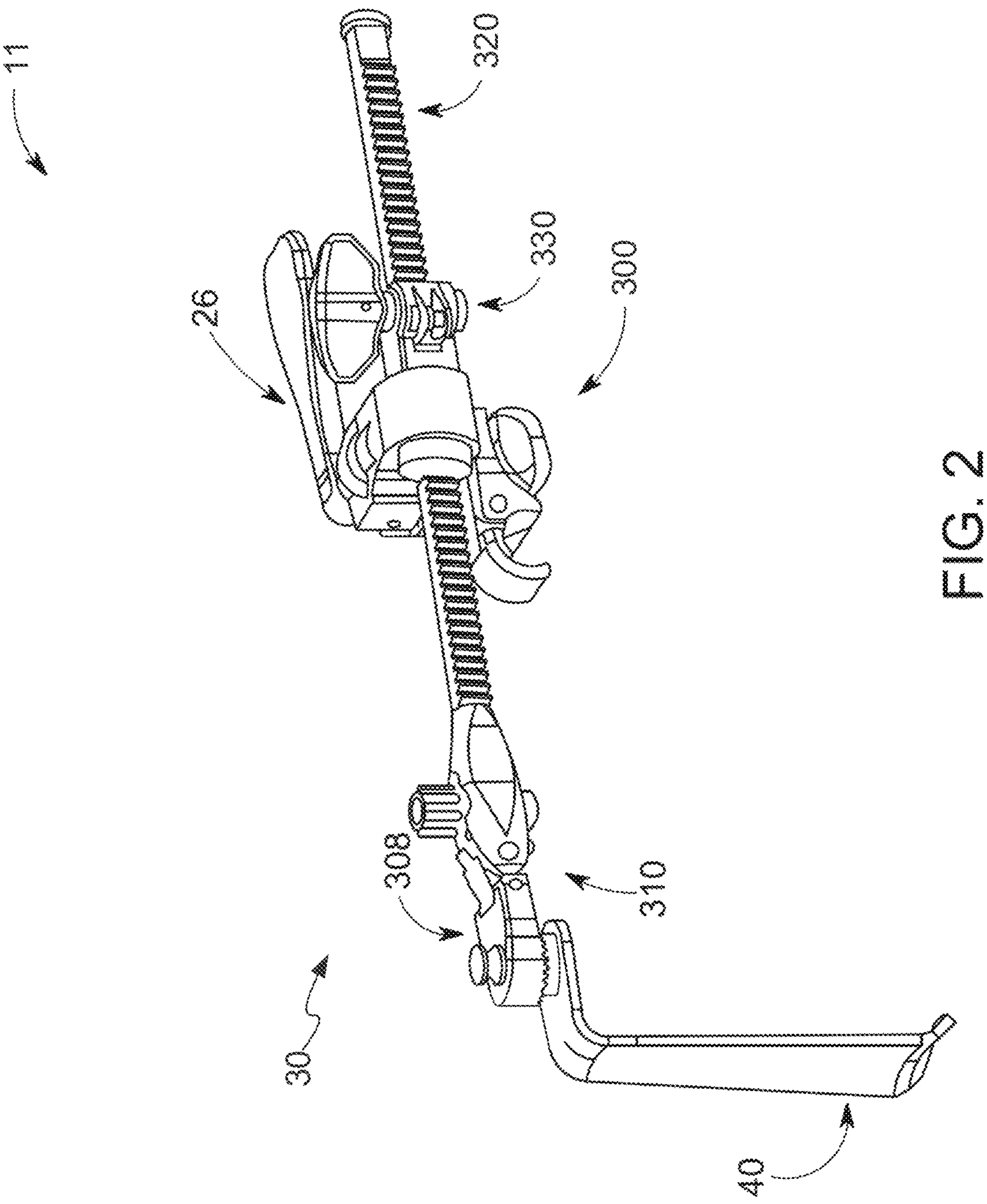
FIG. 2 provides a perspective view for a jointed arm for the retractor system of FIG. 1.

FIG. 2 illustrates a retractor assembly 11 comprising clamp 26, jointed arm 30, and a retractor blade 40 secured to the jointed arm 30. The jointed arm 30 may adjustably constrain a proximal portion of a retractor blade 40 when the retractor blade 40 is secured to the jointed arm 30. In some embodiments, the jointed arm 30 may provide at least some appreciable freedom of motion in at least one direction for the retractor blade 40 relative to the frame assembly 20. While preventing at least some motion of the retractor blade 40, the jointed arm 30 may allow the proximal portion of the retractor blade 40 some freedom of motion but maintain the retractor blade 40 at or near a selected position. In other embodiments, the jointed arm 30 may be adapted to maintain the retractor blade 40 in a fixed or stationary position once various joints are arranged in a desired position.

The illustrated jointed arm 30 is an example of an adjustable arm used to secure a retractor blade 40 to the frame assembly 20. The jointed arm 30 may comprise one or more single-axis hinges, which may be adjusted and then locked to a desired position. However, the jointed arm 30 may comprise other types of adjustable joints. For example, the jointed arm 30 may include one or more universal joints, ball joints, prismatic joints, etc. located along the length of the jointed arm 30.

As shown, the jointed arm 30 may comprise a ratchet 300 having a rack 320 and a pinion 330. A retractor connector 308 of the jointed arm 30 may be adjoined to a distal portion of the rack 320 via a pivot joint 310. The rack 320 may include teeth adapted to engage the pinion 330. The ratchet 300 may also include a clamp 26 that may be used to secure the jointed arm 30 to a frame member 24. Furthermore, the retractor connector 308 of the jointed arm may be adapted to receive and secure the retractor blade 40 to the distal portion of rack 320.

Rotation of the pinion 330 may effectively extend and/or retract the distal portion of the rack 320 with respect to the frame member 24. Namely, rotation of the pinion 330 in a first direction may extend the distal portion of the rack 320 and the retractor blade 40 attached thereto away from the frame member 24. Conversely, rotation of the pinion 330 in a second direction opposite the first direction may retract the distal portion of the rack 320 and the retractor blade 40 attached thereto toward the frame member 24.

Referring now to FIGS. 3-11, aspects of an embodiment of a ratchet 500 are shown. In various embodiments, the jointed arm 30 may be implemented with the ratchet 500 of FIGS. 3-11 instead of the ratchet 300 of FIG. 2 The ratchet 500 may include a ratchet body 510, a rack 520, a pinion 530, a handle 540, a cam disc 550, a release button 560, and pawls 570. A clamp (not shown) similar to the clamp 26 of FIG. 2 may be integrated or otherwise secured to the ratchet body 510. For example, a clamp may be integrated or secured to a bottom side of the ratchet body 510, which is opposite the release button 560. Via such clamp, the ratchet 500 and an associated retractor blade 40 may be secured to a frame member 24.

In general, the pawls 570 of the ratchet 500 may be biased to a locked position in which the pawls 570 via their engagement with the rack 520 may prevent movement of the ratchet body 510 along the rack 520. Pressing the release button 560 may move the pawls 570 to an unlocked position in which the pawls 570 are released from the rack 520 and permit the ratchet body 510 to travel along the rack 520. Moreover, the pinion 530 and cam disc 550 may cooperate to selectively release the pawls 570 from the rack 520 and impart ratcheted movement of the ratchet body 510 along the rack 520 through rotation of the handle 540. In particular, rotation of the handle 540 may rotate the pinion 530 and the cam disc 550. Due to such rotation, the cam disc 550 may periodically release the pawls 570 from the rack 520. Further, rotation of the pinion 530 may cause the pinion 530 to engage teeth of the rack 520 and impart movement of the ratchet body 510 along the rack 520 during the periodic release of the pawls 570 from the rack 520.

Figure 3:
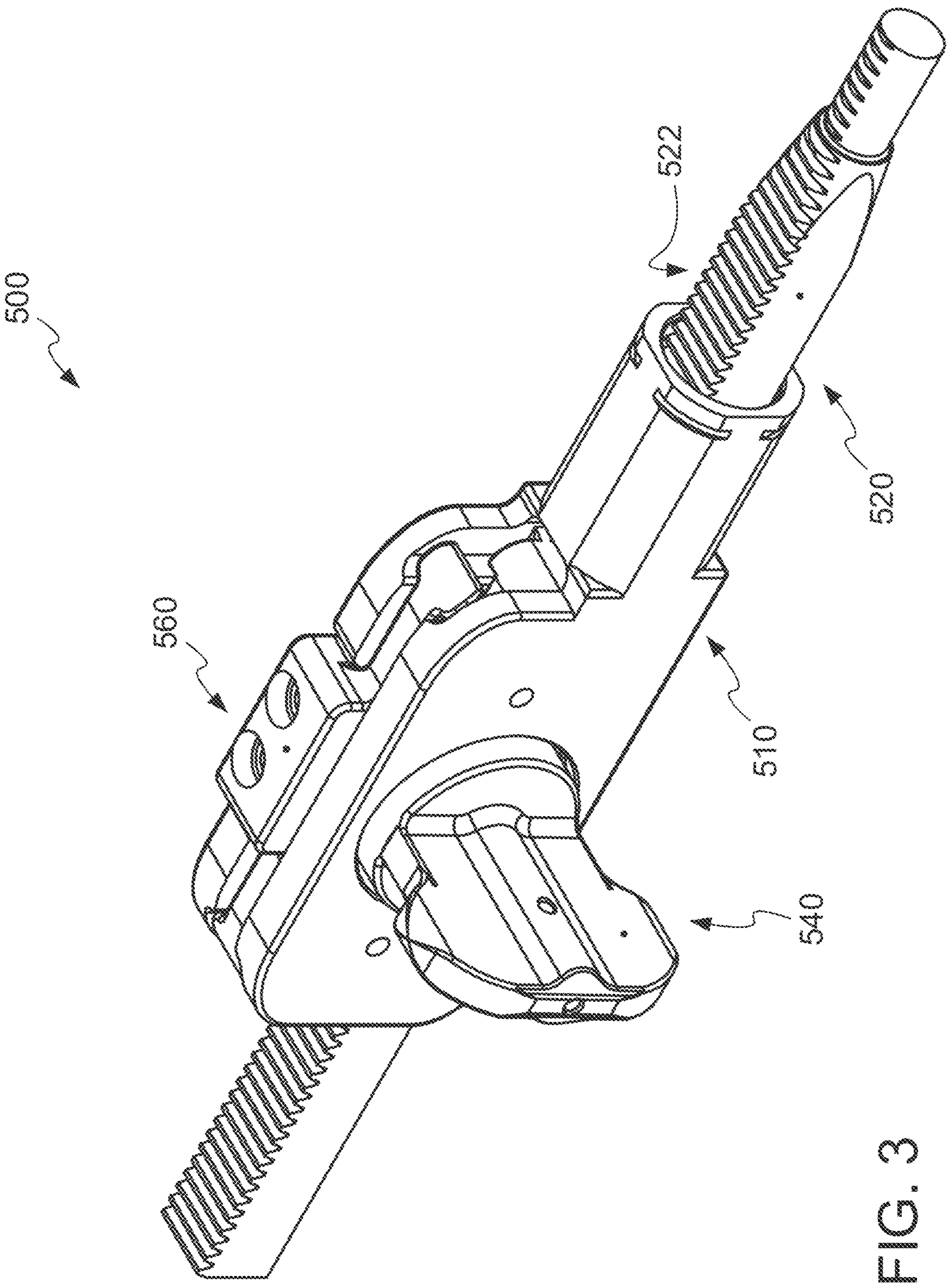
FIG. 3 provides a perspective view for a ratchet for the jointed arm of FIG. 2.
Figure 4A:
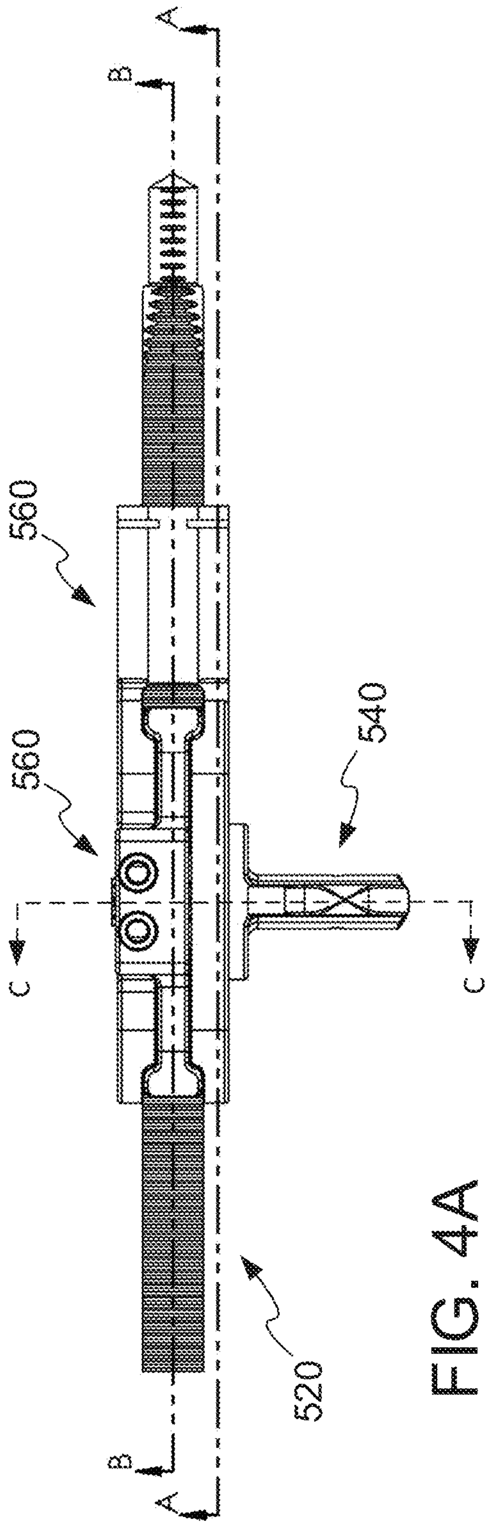
FIGS. 4A-4D provide a top view and respective cross sections for the ratchet of FIG. 3.
Figure 4B:
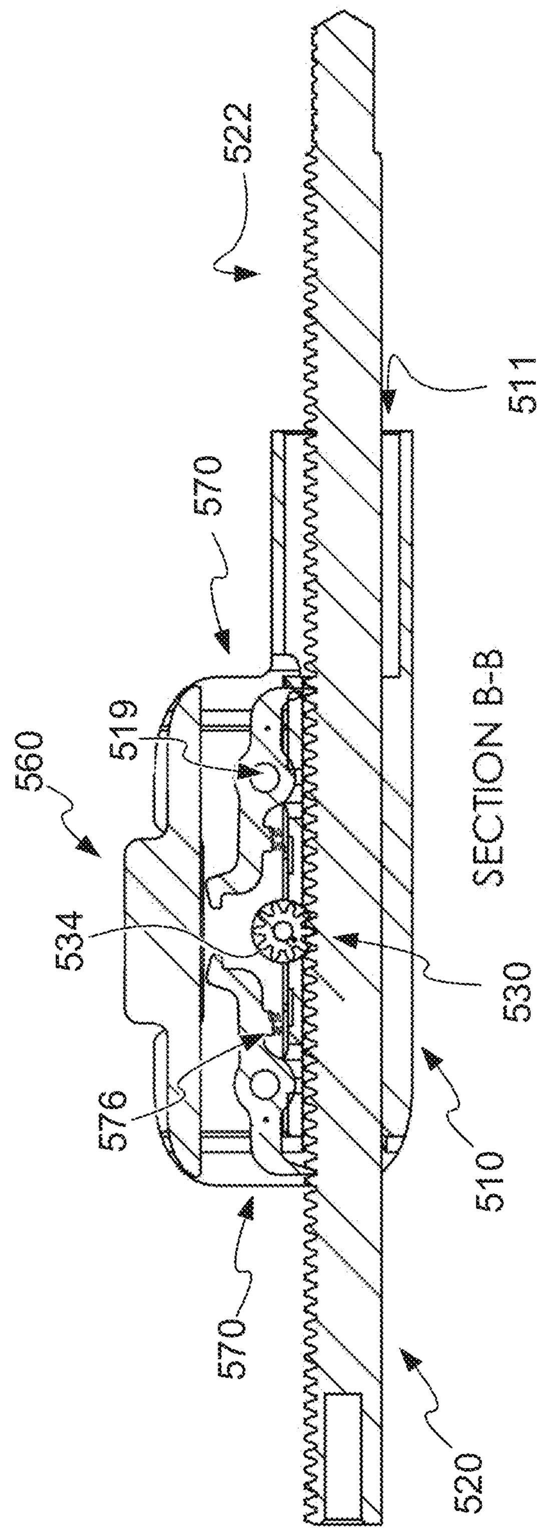
Figure 4C:
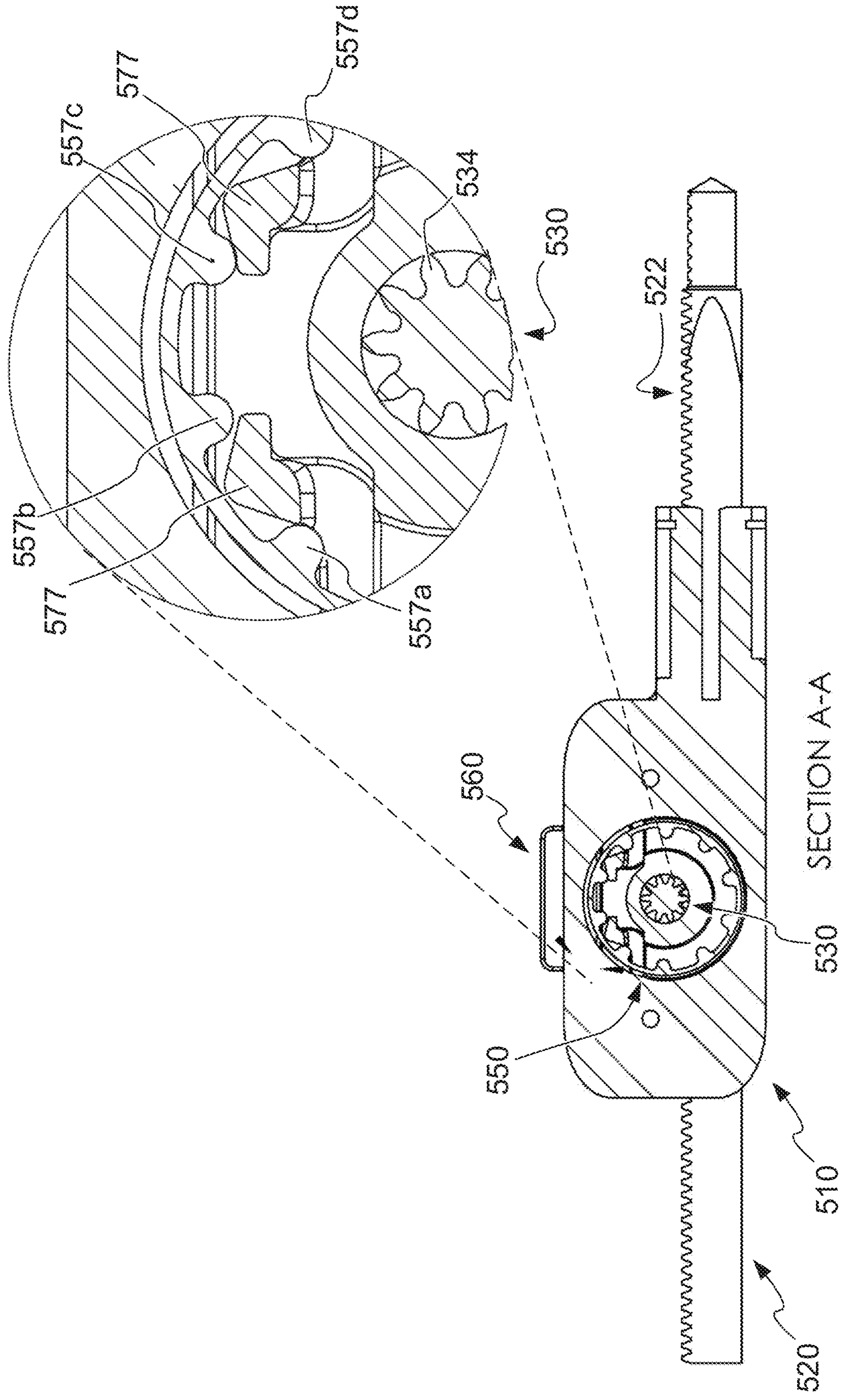

As shown in FIGS. 3-4C, the rack 520 may comprise a cylindrical rod or rail having a rectangular cross section. Moreover, the rack 520 may include rack teeth 522 spanning a longitudinal surface of the rack 520. While not depicted, the rack 520 may include a stop toward a free end that prevents accidental removal of the rack 520 from the ratchet body 510.

Figure 5A:
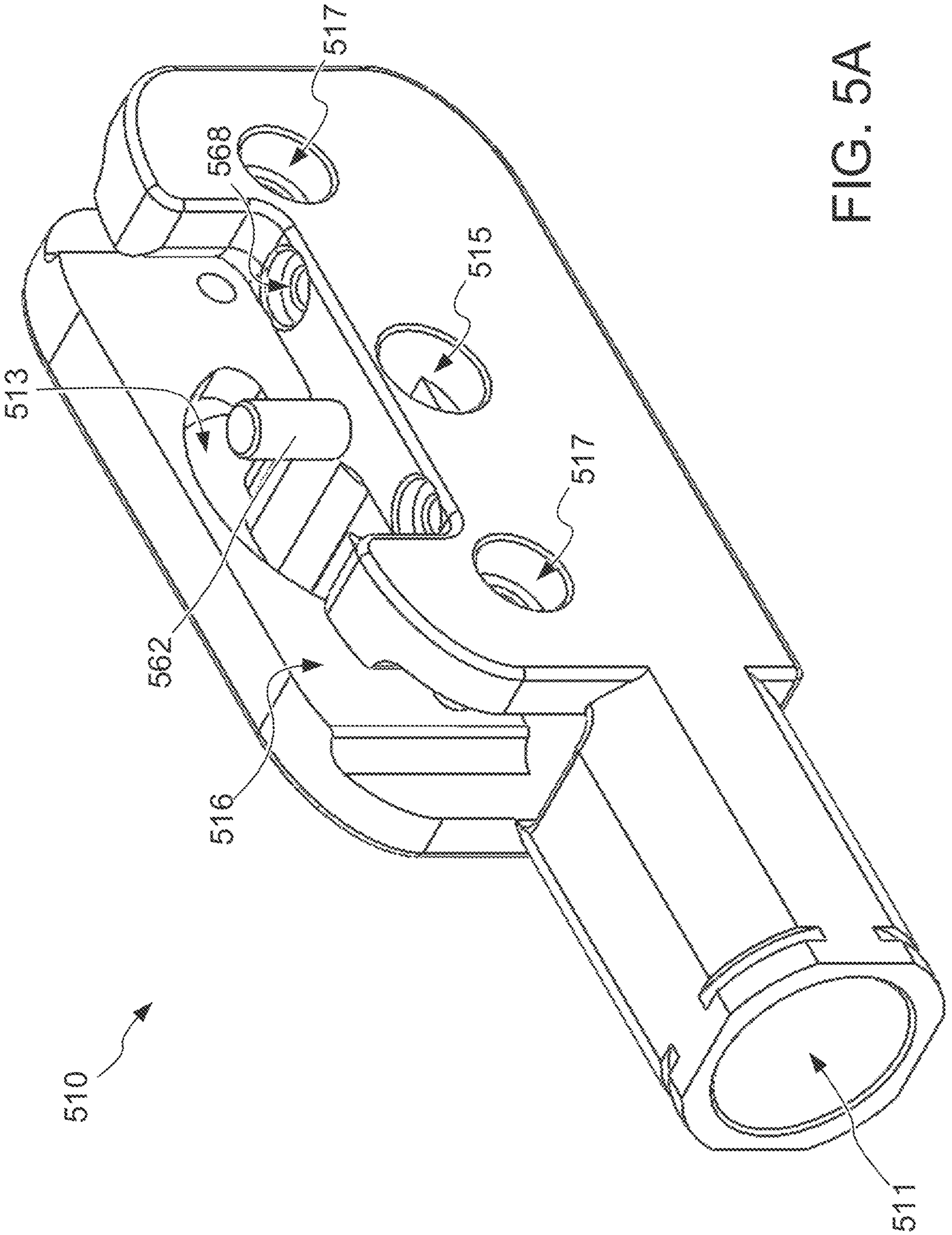
FIGS. 5A and 5B provide a perspective views for a ratchet body of the ratchet of FIG. 3.
Figure 5B:
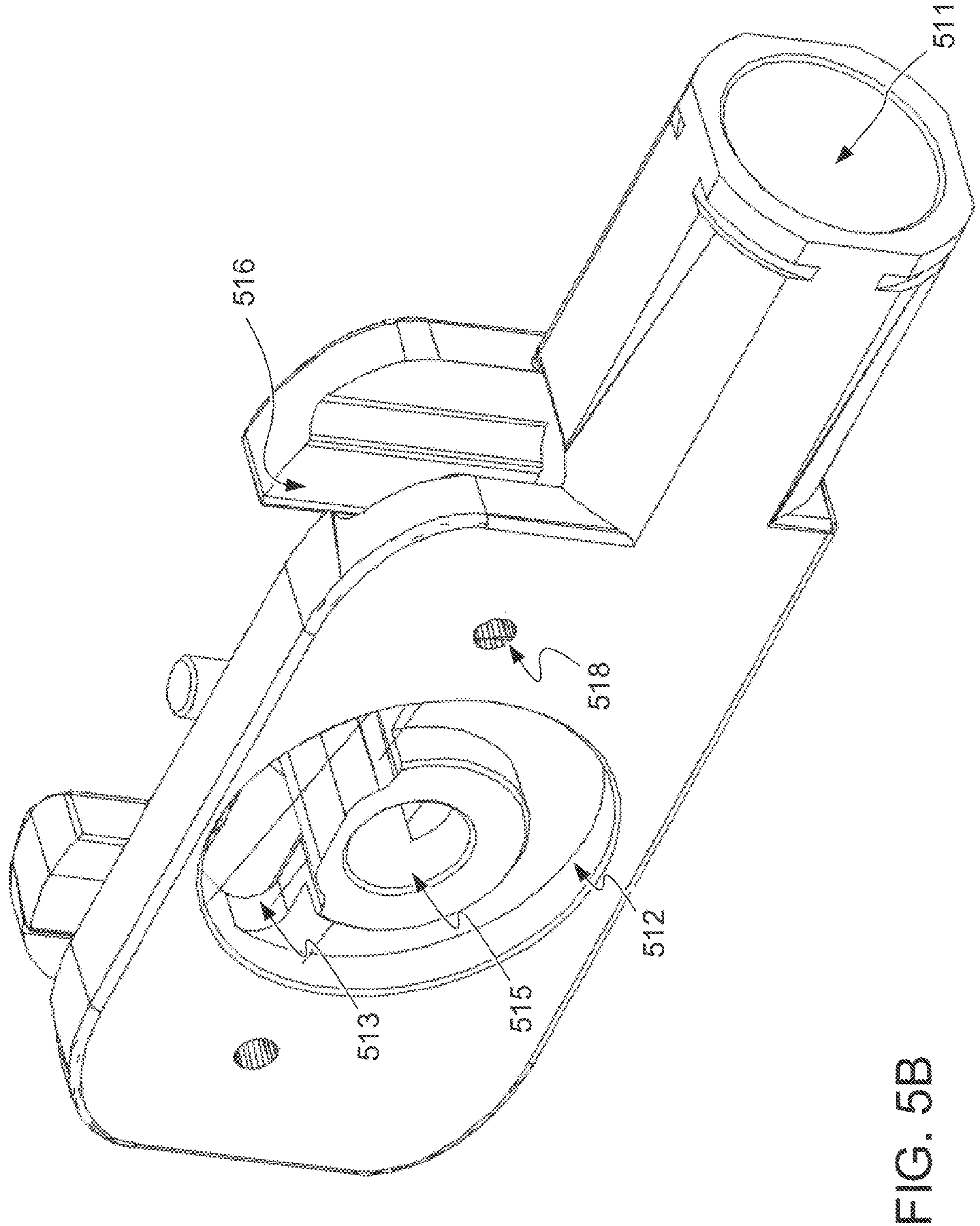

Referring to FIGS. 5A and 5B, the ratchet body 510 may include a rack aperture 511 that passes between longitudinal ends of the ratchet body 510. The rack aperture 511 may be sized to receive the rack 520 and may permit longitudinal passage of the rack 520 through the ratchet body 510.

A first lateral side of the ratchet body 510 may include an annular recess 512. The annular recess 512 may receive and closely mate with the cam disc 550. In particular, the annular recess 512 may have an outer diameter slightly larger than an outer diameter of the cam disc 550 and an inner diameter slightly smaller than an inner diameter of the cam disc 550. In this manner, the annular recess 512 may receive the cam disc 550 and permit rotation of the cam disc 550 about a rotational axis while limiting radial movement of the cam disc 550. As further shown, the first lateral side of the ratchet body 510 may include a pawl aperture 513. The pawl aperture 513 may pass through a bottom surface of the annular recess 512. As explained in greater detail below, pawl tabs 577 may pass through the pawl aperture 513 to permit engagement of protrusions along an inner surface of the cam disc 550 with the pawl tabs. In particular, protrusions may periodically engage pawl tabs 577 and release the pawls 570 from the rack 520. Further, the ratchet body 510 may include a pinion hole 515 that passes through the first lateral side of the ratchet body 510 and a second lateral side of the ratchet body 510, which is opposite the first lateral side of the ratchet body 510. The pinion hole 515 may be sized to receive and closely mate with the pinion 530. In particular, the diameter of the pinion hole 515 may be slightly larger than a diameter of the pinion 530.

A top side of the ratchet body 510 may include a top side recess 516 sized to hold the release button 560 and the pawls 570. In particular, internal sidewalls of the top side recess 516 may mate with longitudinal sides of the release button 560 and the pawls 570.

Further, the ratchet body 510 may include pawl fastener holes 517 through the second lateral side of the ratchet body 510 and may include bores 518 in the first lateral side of the ratchet body 510. Pivot fasteners 519 may pass through pawl fastener holes 517, pawl pivot holes 572, and into the bores 518. The pivot fasteners 519 may secure the pawls 570 in the top side recess 516. In various embodiments, the pivot fasteners 519 may be screws. However, as used herein, fasteners may include various types of mechanical fasteners such as screws, bolts, threaded rods, rivets, pins, clevis pins, etc.

Each pawl 570 may rotate about its respective pivot fastener 519. In particular, each pawl 570 may be rotated between a locked position and an unlocked position. Rotation of a pawl 570 toward its locked position may rotate its pawl distal portion 573 toward the rack 520 and engage one or more rack teeth 522 with the pawl distal portion 573. Conversely, rotation of a pawl 570 toward its unlocked position may rotate its pawl distal portion 573 away from the rack 520 and release the pawl distal portion 573 from the rack teeth 522.

In some embodiments, the unlocked position may disengage the pawl distal portions 573 from the rack teeth 522 such that the pawl distal portions 573 do not contact the rack teeth 522 thus permitting the ratchet body 510 to travel along the rack 520. However, in some embodiments, the pawl distal portions 573 when in the unlocked position may remain in contact with the rack teeth 522 or may make periodic contact with the rack teeth 522 as the ratchet body 510 travels along the rack 520. In such embodiments, the pawl distal portions 573 may be sufficiently moved away from the rack 520 and/or a biasing force may be sufficiently reduced to permit the pawl distal portions 573 to pass over the rack teeth 522 despite contacting the rack teeth 522.

A spring 576 may be positioned between each pawl proximal portion 578 and a bottom surface of the top side recess 516. See, e.g., FIG. 4B. In some embodiments, the pawl proximal portion 578 and/or the top side recess 516 may include a spring seat (e.g., recess, posts, tabs, etc.) that may help maintain the spring 576 at a desired position between the pawl 570 and the ratchet body 510. Each spring 576 may provide a spring force that biases its respective pawl proximal portion 578 away from the bottom surface of the top side recess 516. Such biasing of the pawl proximal portion 578 may further bias the pawl distal portion 573 toward the rack teeth 522 due to pivoting about its pivot fasteners 519. Moreover, in various embodiment, a bottom surface of the release button 560 may rest on the pawl proximal portions 578. As such, the springs 576 may further bias the release button 560 outwardly from the top side recess 516.

The ratchet body 510 may further include a button post 562. The button post 562 may protrude above a bottom surface of the top side recess 516. The button post 562 may have a cylindrical shape and may be sized to closely mate with an aperture 566 of the release button 560. See, e.g., FIG. 4C. However, in some embodiments, the post and aperture may be reversed. Namely, the bottom surface of the top side recess 516 may have an aperture to receive a post protruding from a bottom side of the release button 560.

The release button 560 may comprise a button body 561 and button tabs 563 that longitudinally protrude from the button body 561. See, e.g., FIG. 8. In particular, each button tab 563 may be coupled to (or integrated with) the button body 561. Each button tab 563 may be keyed to closely mate with lateral sides of the top side recess 516. In particular, a distal portion of each button tab 563 may have a wider lateral width than a proximal portion. The release button 560 may further include fastener holes 564 that pass vertically through the button body 561. Button fasteners 569 may pass through the fastener holes 564 and into bores 568 in a bottom surface of the top side recess 516. Such features of the release button 560 may help prevent the release button 560 from rotating about button post 562 and/or may help prevent the button tabs 563 from appreciably teeter-tottering about the button post 562 when the release button 560 is pressed into the top side recess 516.

Figure 6:
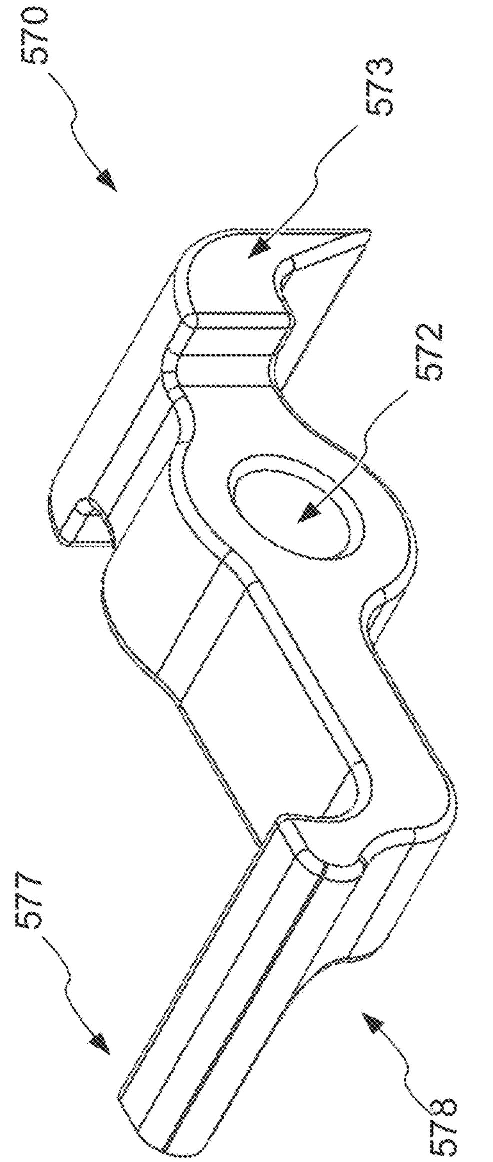
FIGS. 6 and 7 provide perspective views for pawls of the ratchet of FIG. 3.
Figure 7:
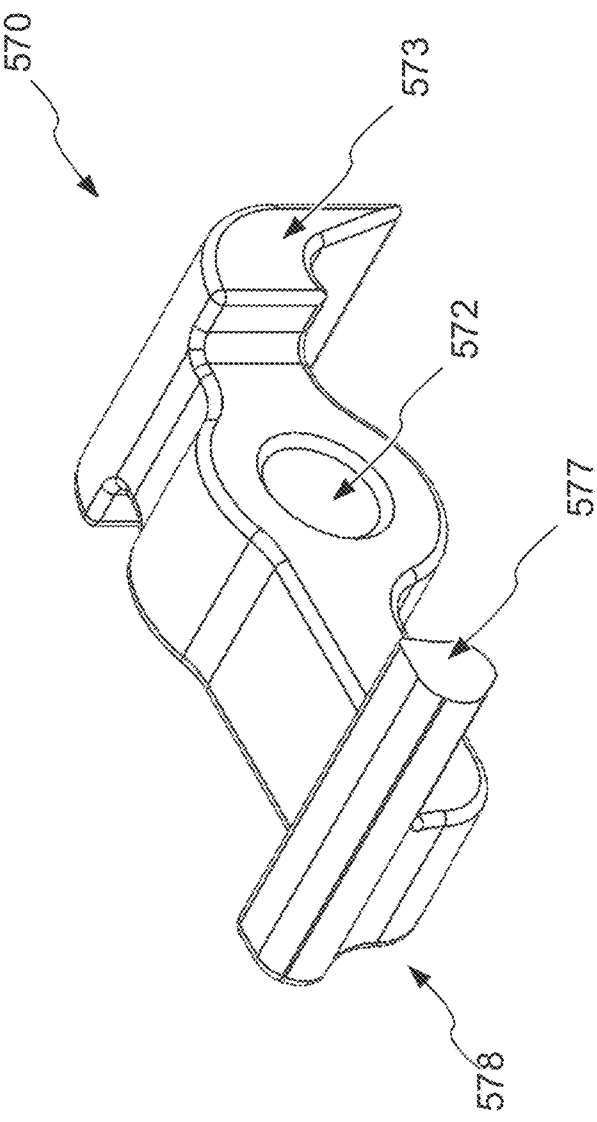
Figure 8:
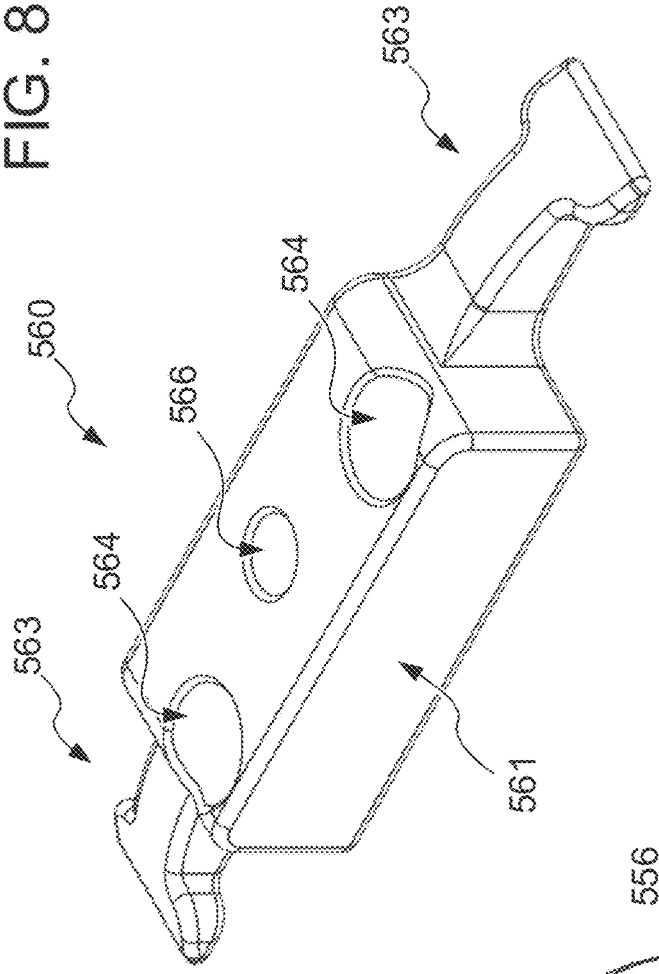
FIG. 8 provides a perspective view for a release button of the ratchet of FIG. 3.

As noted above, each pawl 570 may include a pawl pivot hole 572, a pawl proximal portion 578, and a pawl distal portion 573. In some embodiments, the pawls 570 are implemented as mirror images of one another. In particular, FIG. 6 depicts a fore pawl (e.g., the right pawl of FIGS. 3-4C), and FIG. 7 depicts an aft pawl (e.g., the left pawl of FIGS. 3-4C). The pawl proximal portion 578 may include a pawl tab 577 that extends from a lateral side of the pawl 570. When assembled, the pawl tabs 577 may extend through the pawl aperture 513 and into the cam disc recess 556. Cam disc protrusions 557 along inner walls of the cam disc recess 556 may engage the pawl tabs 577. In particular, the cam disc protrusions 557 are positioned such that the cam disc protrusions 557 periodically press the pawl tabs 577 and release the pawl distal portions from the rack teeth 522 as the cam disc 550 rotates in either direction. As such, the ratchet 500 may provide bi-directional ratcheted movement of the ratchet body 510 along the rack 520.

Figure 11:
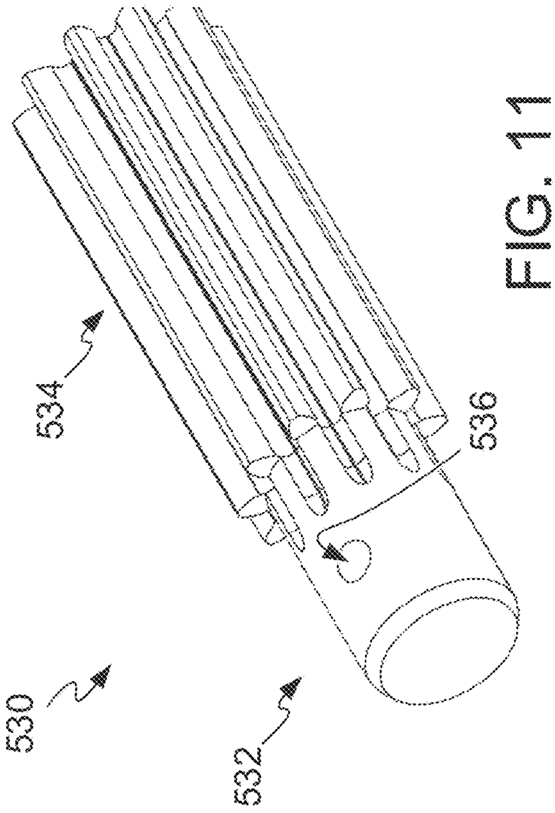
FIG. 11 provides a perspective view for a pinion of the ratchet of FIG. 3.

As shown in FIG. 11, the pinion 530 may include a central axel 532 and teeth 534 that extend radially from the central axel 532. The teeth 534 may be sized to engage and closely mesh with rack teeth 522 as the pinion 530 rotates in the pinion hole 515 about its longitudinal axis. Moreover, the central axel 532 may include a retaining pin hole 536 that pass laterally through a proximal portion of the central axel 532. Such retaining pin hole 536 may be used to secure the pinion 530 to handle 540 so that rotation of the handle 540 rotates the pinion 530. The pinion 530 may include a bore 538 that extends longitudinally into the distal end of the pinion 530. See, e.g., FIG. 4C.

Figure 4D:
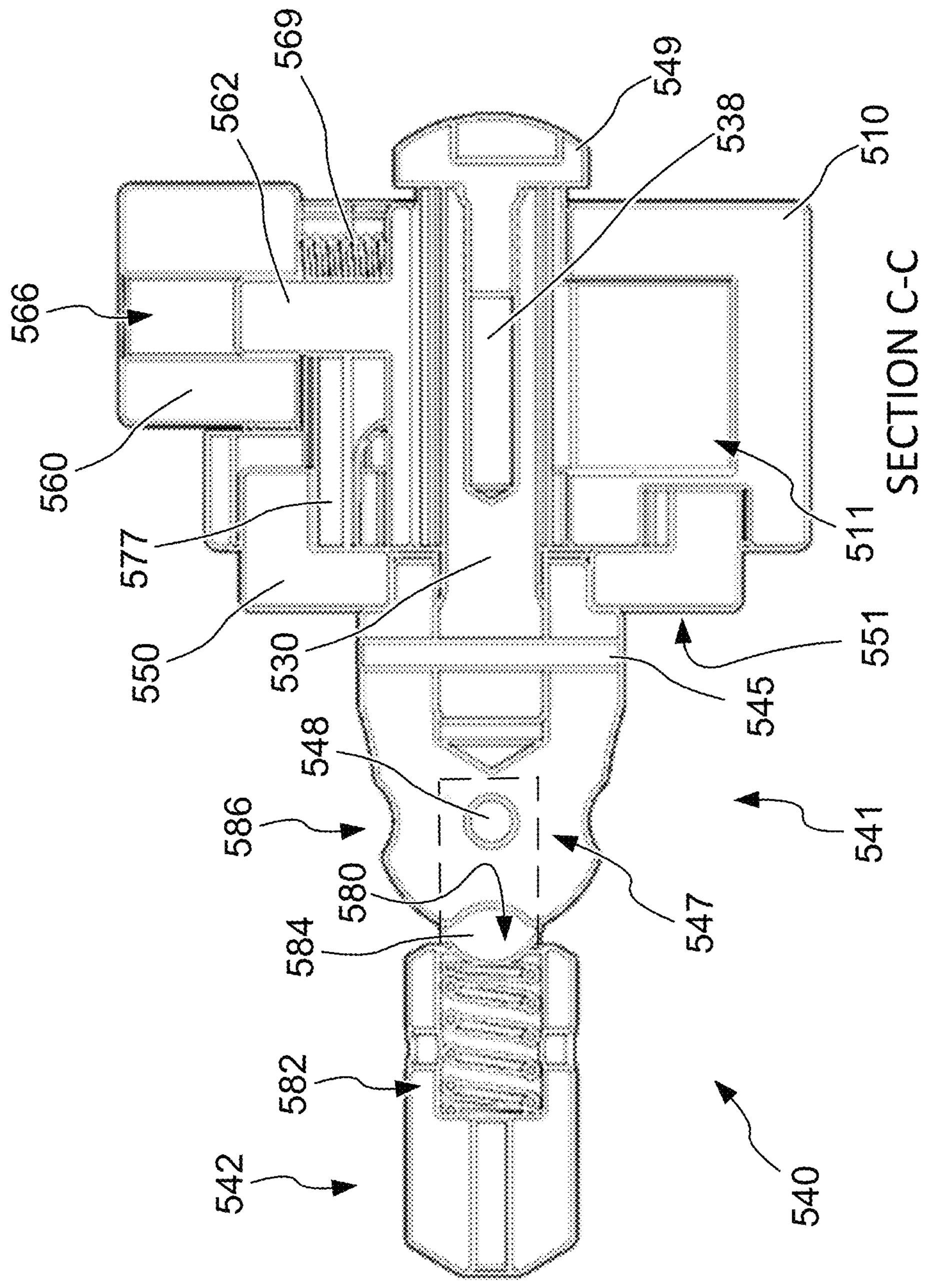
Figure 10:
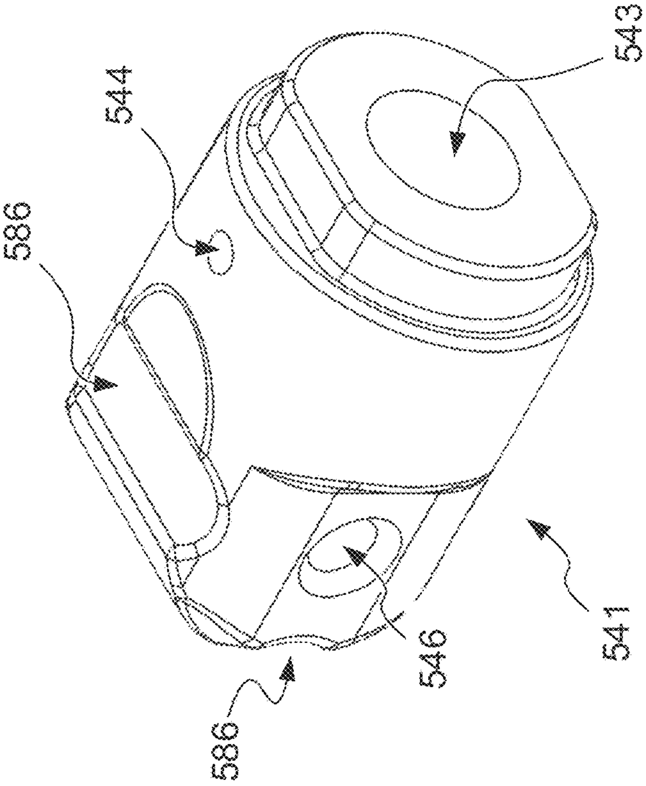
FIG. 10 provides a perspective view for a handle stem used in an embodiment of the ratchet of FIG. 3.

Referring now to FIGS. 4D, 10, and 11, the handle 540 may include a handle stem 541 and a handle grip 542. The handle stem 541 may include an axel bore 543 that extends longitudinally into a distal end of the handle stem 541. The axel bore 543 may be sized to receive and closely mate with the central axel 532 of the pinion 530. The handle stem 541 may have an diameter that is larger than the pinion hole 515 that passes though the ratchet body 510. A distal portion of the handle stem 541 may include a first retaining pin hole 544 that passes laterally through the stem 541. As noted above, the central axel 532 may include the retaining pin hole 536 that passes laterally through the central axel 532. A retaining pin 545 may pass through the retaining pin holes 536, 544 and secure the central axel 532 of the pinion 530 to the handle stem 541.

A proximal portion of the handle stem 541 may include a second retaining pin hole 546 that passes laterally through the handle stem 541. Similarly, a distal portion of the handle grip 542 may include a retaining pin hole 547 that passes laterally through the handle grip 542. A retaining pin 548 may pass through the retaining pin holes 546, 547 and secure the distal portion of the handle grip 542 to the proximal portion of the handle stem 541.

The handle grip 542 may include a bore 580 that extends longitudinally into its distal end. The bore 580 may be sized to receive a spring 582 used to bias detent 584 that is trapped between the distal end of the handle grip 542 and the proximal end of the handle stem 541. The handle stem 541 may also include indentations 586 in its proximal end and along lateral sides of its proximal portions. Such indentations 586 may be sized to receive an outer surface of the detent 584. In such an embodiment, the handle grip 542 may pivot about the retaining pin 548 and the spring-bias detent 584 may engage indentations 586 in the handle stem 541. As such, the handle grip 542 may be pivoted between respective indentations 586 which effectively hold the handle grip 542 in the respective pivoted position.

In the embodiment of FIG. 4D, the handle grip 542 may be pivoted with respect to the handle stem 541. However, in other embodiments, the handle grip 542 may be affixed to or integrated with the handle stem 541 to provide a handle 540 with a fixed handle grip that does not pivot with respect to its handle stem 541. See, e.g., FIG. 3.

As shown in FIG. 4D, a fastener 549 may pass through the pinion hole 515 in the second lateral side of the ratchet body 510 and into the bore 538 of the pinion 530. In the depicted embodiment, a head of the fastener 549 has a larger diameter than the pinion hole 515. In some embodiments, a washer having a larger diameter than the pinion hole 515 may be placed between the head of the fastener 549 and the second lateral side of the ratchet body 510. As noted above, the handle stem 541 has a larger diameter than the pinion hole 515. Thus, once assembled, the pinion 530 may be trapped between the handle stem 541 and the fastener 549 and retained in the pinion hole 515 of the ratchet body 510. Due to such arrangement, the handle 540 via the handle stem 541 may rotate the pinion 530 in the pinion hole 515 of the ratchet body 510.

Figure 9:
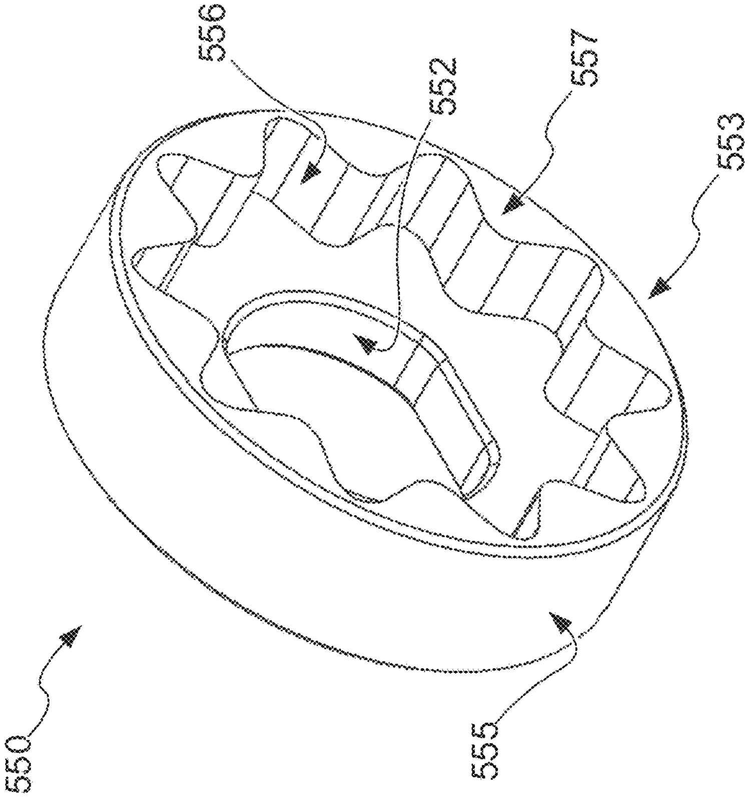
FIG. 9 provides a perspective view for a cam disc of the ratchet of FIG. 3.

As further shown in FIGS. 9 and 10, the distal portion of the handle stem 541 may be keyed to closely mate with a keyed surfaces 552 of a cam disc first side 551. Due to such keying, rotation of the handle stem 541 about its longitudinal axis may rotate the cam disc 550 in unison with the handle stem 541. The keyed surfaces 552 are depicted as an aperture through the cam disc first side 551, which has a circular shape with flat portions. However, other embodiments may utilize keyed surfaces of a recess and/or keyed surfaces having of various shapes (e.g., hexagonal, cross, star, etc.) that are suitable for ensuring rotation of the handle stem 541 results in rotation of the cam disc 550.

As shown in FIG. 9, the cam disc 550 may a have generally cylindrical shape comprising a cam disc first side 551, a cam disc second side 553 opposite the cam disc first side 551, and a cam disc lateral side 555 adjoining the cam disc first side 551 and the cam disc second side 553. The cam disc first side 551 may include keyed surfaces 552 sized to receive and closely mate with the keyed portion of the handle stem 541. The cam disc second side 553 may include a cam disc recess 556. As shown, an inner wall of the cam disc recess 556 may include cam disc protrusions 557.

Referring now to the magnified portion of FIG. 4C, the diameter of the cam disc recess 556 and the spacing of the cam disc protrusions 557 along its inner wall ensure that the cam disc protrusions 557 simultaneous (or nearly so) engage the pawl tabs 577. If the cam disc 550 rotates clockwise in FIG. 4C, the cam disc protrusion 557*a* engages the pawl tab 577 of the aft pawl 570 and the cam disc protrusion 557*c* engages the pawl tab 577 of the fore pawl 570. If the cam disc 550 continues to rotate in the clockwise direction, the cam disc protrusions 557*a*, 557*c* force their respective pawl tabs 577 downward thus retracting the pawl distal portions 573 from the rack 520 and permitting the pawl distal portions 573 to pass over rack teeth 522 as the ratchet body 510 travels toward the fore end of the rack 520. If the cam disc 550 continue to rotate in the clockwise direction, the cam disc protrusions 557*a*, 557*c* eventually disengage their respective pawl tabs 577 thus permitting the pawl distal portions 573 via their spring bias to return to their locked position. Thus, without further rotation of the cam disc 550 or pressing of the release button 560, the pawls 570 may prevent further movement of the ratchet body 510 toward either the fore or aft end of the rack 520.

Conversely, if the cam disc 550 rotates counterclockwise in FIG. 4C, the cam disc protrusion 557*b* engages the pawl tab 577 of the aft pawl 570 and the cam disc protrusion 557*d* engages the pawl tab 577 of the fore pawl 570. If the cam disc 550 continues to rotate in the counterclockwise direction, the cam disc protrusions 557*b*, 557*d* force their respective pawl tabs 577 downward thus releasing the pawl distal portions 573 from the rack 520 and permitting the pawl distal portions 573 to pass over rack teeth 522 as the ratchet body 510 travels toward the aft end of the rack 520. If the cam disc 550 continues to rotate in the counterclockwise direction, the cam disc protrusions 557*b*, 557*d* eventually disengage their respective pawl tabs 577 thus permitting the pawl distal portions 573 via their spring bias to return to their locked position. Thus, without further rotation of the cam disc 550 or pressing of the release button 560, the pawls 570 may prevent further movement of the ratchet body 510 toward either the fore or aft end of the rack 520.

In the above manner, the cam disc 550 via the cam disc protrusions 557 may selectively and simultaneously release both pawls 570 so as to permit ratcheted movement in either direction. While the cam disc 550 may simultaneously release both pawls 570 from the rack 520 in the depicted embodiment, in some embodiments the cam disc protrusions 557 do not release the pawls 570 exactly at the same time. The trailing pawl 570 may naturally rotate away from the rack teeth 522 and overcome its spring bias when the ratchet body 510 moves along the rack 520 in a direction away from the trailing pawl 570. Thus, the cam disc protrusions 557 may engage and unlock the leading pawl 570 to effectuate ratcheted movement in the direction away from the trailing pawl even if the cam disc protrusions 557 do not release the trailing pawl 570 or are slightly delayed in their release of the trailing pawl 570. Due to such functioning of the trailing pawl 570, there is some built-in tolerance to the design. Namely, the cam disc protrusions 557 and the diameter of the cam disc recess 556 need to exactly align the cam disc protrusions 557 for simultaneous engagement of the pawl tabs 577.

While the foregoing has been described with reference to certain aspects and examples, various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular example(s) disclosed, but that the disclosure includes all embodiments falling within the scope of the appended claims.

What is claimed is:

1. A retractor system for use with a frame member, the retractor system comprising:

a ratchet comprising a ratchet body, a rack comprising a rack first end, a rack second end, and rack teeth along a surface of the rack between the rack first end the rack second end, a pinion engaged with the rack teeth, a first pawl engaged with the rack teeth, a second pawl engaged with the rack teeth, a cam disc comprising cam disc protrusions, and a handle coupled to the pinion and the cam disc;

a retractor connector coupled to the rack first end and configured to receive a retractor blade and secure the retractor blade to the rack; and a clamp coupled to the ratchet body and configured to secure the ratchet body to the frame member;

wherein rotation of the handle rotates the pinion and the cam disc;

wherein rotation of the cam disc causes the cam disc protrusions to engage the first pawl and the second pawl and release the first pawl and the second pawl from the rack teeth; and wherein rotation of the pinion imparts movement of the ratchet body along the rack.

2. The retractor system of claim 1, comprising one or more springs that bias the first pawl and the second pawl toward engagement with the rack teeth.

3. The retractor system of claim 2, wherein rotation cam disc causes of the cam disc protrusions to disengage the first pawl and the second pawl and permit the one or more springs to bias the first pawl and the second pawl toward engagement with the rack teeth.

4. The retractor system of claim 1, comprising a release button that in response to being pressed disengages the first pawl and the second pawl from the rack teeth.

5. The retractor system of claim 1, wherein the cam disc protrusions are spaced in a manner that periodically engages and disengages the first pawl and the second pawl from the rack teeth as the rack traverses through the ratchet body.

6. The retractor system of claim 1, wherein the cam disc protrusions are spaced in a manner that periodically moves portions of the first pawl and the second pawl that engage the rack teeth in a direction away from the rack teeth.

7. The retractor system of claim 1, wherein the cam disc protrusions are spaced in a manner that periodically permits the first pawl and the second pawl to pass over the rack teeth.

8. The retractor system of claim 1, wherein:
the cam disc comprises a cam disc recess;
the cam disc protrusions are along an inner wall of the cam disc recess;
the first pawl comprises a first pawl tab that extends into the cam disc recess and engages one or more of the cam disc protrusions; and
the second pawl comprises a second pawl tab that extends into the cam disc recess and engages one or more of the cam disc protrusions.

9. A retractor system, comprising:
a frame assembly comprising one or more posts and one or more frame members coupled to the one or more posts;
a ratchet coupled to the one or more frame members, the ratchet comprising a rack, a pinion, a first pawl, a second pawl, a cam disc, and a handle; and
a retractor blade coupled to a first end of the rack;
wherein the handle is coupled to the pinion and the cam disc such that rotation of the handle rotates the cam disc and pinion;
wherein rotation of the cam disc causes the cam disc to engage the first pawl and the second pawl and release the first pawl and the second pawl from the rack; and
wherein rotation of the pinion imparts ratchet movement of the rack and the retractor blade with respect to the one or more frame members.

10. The retractor system of claim 9, comprising one or more springs that bias the first pawl and the second pawl toward engagement with the rack.

11. The retractor system of claim 10, wherein rotation of the cam disc causes the cam disc to disengage the first pawl and the second pawl and permit the one or more springs to bias the first pawl and the second pawl toward engagement with the rack.

12. The retractor system of claim 9, wherein the ratchet comprises a release button that in response to being pressed move portions of the first pawl and the second pawl that engage the rack in a direction away from the rack.

13. The retractor system of claim 9, wherein the cam disc comprises cam disc protrusions that are spaced to periodically engage and disengage the first pawl and the second pawl from the rack as the cam disc is rotated.

14. The retractor system of claim 9, wherein the cam disc comprises cam disc protrusions that are spaced to periodically move portions of the first pawl and the second pawl that engage the rack in a direction away from the rack as the cam disc is rotated.

15. The retractor system of claim 9, wherein the cam disc comprises cam protrusions that are spaced to periodically permit the first pawl and the second pawl to pass over the rack as the cam disc is rotated.

16. The retractor system of claim 9, wherein:
the cam disc comprises a cam disc recess and cam disc protrusions along an inner wall of the cam disc recess;
the first pawl comprises a first pawl tab that extends into the cam disc recess and engages one or more of the cam disc protrusions; and
the second pawl comprises a second pawl tab that extends into the cam disc recess and engages one or more of the cam disc protrusions.

17. A retractor system, comprising:
a ratchet comprising a ratchet body, a rack that passes through the ratchet body, a pinion that engages rack teeth of the rack, a first pawl comprising a first pawl distal portion that engages the rack teeth, a second pawl comprising a second pawl distal portion that engages the rack teeth, a cam disc, and a handle; and
a retractor blade coupled to a first end of the rack;
wherein the handle is coupled to the pinion and the cam disc and rotates the pinion in unison with the cam disc; and
wherein rotation of the cam disc causes the cam disc to press a first pawl proximal portion of the first pawl and a second pawl proximal portion of the second pawl which causes the first pawl distal portion and the second pawl distal portion to pivot away from the rack teeth; and
wherein rotation of the pinion moves the ratchet body along the rack.

18. The retractor system of claim 17, comprising one or more springs that bias the first pawl and the second pawl such that the first pawl distal portion and the second pawl distal portion pivot towards the rack teeth.

19. The retractor system of claim 17, wherein the ratchet comprises a release button that presses the first pawl proximal portion and the second pawl proximal portion and causes the first pawl distal portion and the second pawl distal portion to pivot away from the rack teeth.

20. The retractor system of claim 17, wherein:
the cam disc comprises a cam disc recess and cam disc protrusions along an inner wall of the cam disc recess;
the first pawl proximal portion comprises a first pawl tab that extends into the cam disc recess and engages one or more of the cam disc protrusions; and
the second pawl proximal portion comprises a second pawl tab that extends into the cam disc recess and engages one or more of the cam disc protrusions.

* * * * *